United States Patent
Yamamatsu et al.

[11] Patent Number: 5,191,116
[45] Date of Patent: Mar. 2, 1993

[54] PROCESS FOR THE PREPARATION OF METHACRYLIC ACID AND METHACROLEIN

[75] Inventors: Setsuo Yamamatsu; Tatsuo Yamaguchi, both of Fuji, Japan

[73] Assignee: Asahi Kasei Kogyo Kabushiki Kaisha, Osaka, Japan

[21] Appl. No.: 400,117
[22] PCT Filed: May 22, 1989
[86] PCT No.: PCT/JP89/00510
§ 371 Date: Aug. 21, 1989
§ 102(e) Date: Aug. 21, 1989
[51] Int. Cl.$^5$ ............... C07C 47/22; C07C 57/05; B01J 23/28
[52] U.S. Cl. ........................ 562/549; 568/475
[58] Field of Search ............... 562/549; 568/475

[56] References Cited

U.S. PATENT DOCUMENTS

| | | | |
|---|---|---|---|
| 4,066,704 | 1/1978 | Harris et al. | 562/549 |
| 4,260,822 | 4/1981 | Krieger et al. | 562/549 |
| 4,720,575 | 1/1988 | Gruber | 562/549 X |

FOREIGN PATENT DOCUMENTS 62-132832  6/1987  Japan ................... 562/549

*Primary Examiner*—Arthur C. Prescott
*Attorney, Agent, or Firm*—Birch, Stewart, Kolasch & Birch

[57] ABSTRACT

The present invention is directed to a process for preparing methacrylic acid and methacrolein in one step which comprises subjecting isobutane to catalytic oxidation in the presence of molecular oxygen in the vapor phase, with a catalyst comprising a P and/or As—Mo—V and/or Cu composition containing a heteropoly acid. The catalytic oxidation is performed at a temperature of not greater than 350° C., at which temperature the decomposition of the heteropoly acid is unlikely to occur, preferably at a temperature of not greater than 320° C. By means of this process, methacrylic acid and methacrolein are produced with high productivity and in high yield while maintaining a stable activity of the catalyst for a prolonged period of time.

22 Claims, No Drawings

PROCESS FOR THE PREPARATION OF METHACRYLIC ACID AND METHACROLEIN

TECHNICAL FIELD

The present invention relates to a one-step process for the preparation of methacrylic acid and methacrolein, which comprises subjecting isobutane in the vapor phase to catalytic oxidation. More particularly, the present invention is concerned with a process for preparing methacrylic acid and methacrolein, which comprises subjecting isobutane in the vapor phase to catalytic reaction in the presence of molecular oxygen at a high temperature, using a catalyst comprising a P and/or As—Mo—V and/or Cu composition containing a heteropoly acid, thereby obtaining the desired products in high yield and with high selectivity in one step.

BACKGROUND ART

Heretofore, a saturated hydrocarbon, such as isobutane, has been regarded as being an inert gas. For example, in Japanese Patent Application Laid-open Specification No. 55-2619, there is a description to the effect that isobutane is used as a diluent for a reaction gas in the oxidation of an olefin or an aldehyde. Since isobutane is less reactive, as seen from the above, the conventional processes for the preparation of methacrolein or methacrylic acid from isobutane (see for example, Japanese Patent Application Laid-open Specification No. 58-189130) generally consists in the converting of isobutane to isobutylene by the use of a dehydrogenating catalyst or an oxidative dehydrogenating catalyst, and oxidizing the formed isobutylene to obtain the desired product.

In recent years, researches have been carried out with a one-step conversion process by the oxidation of isobutane to a valuable compound such as methacrolein and methacrylic acid. In British Patent No. 1340891, although the yield is extremely low, there is a description suggesting a one-step process for the production of methacrolein from isobutane by contacting a mixed gas of isobutane and oxygen in the vapor phase with an oxide comprising antimony, molybdenum, etc. However, according to the process of the British patent, methacrylic acid cannot be obtained.

It is U.S. Pat. No. 4,260,822 that first taught a one-step process for the production of methacrylic acid from isobutane. According to the process of the U.S. Patent, methacrylic acid is obtained from isobutane, with a high selectivity, in one step, using a specific catalyst comprising oxides of antimony, molybdenum and phosphorus. For example, when the concentration of isobutane is 10 mol%, 10% of the isobutane participates in the reaction, 50% of which is converted to methacrylic acid. However, under such conditions, the methacrylic acid content of the reaction gas is as low as 0.5 mol %, and accordingly, the productivity per unit weight of the catalyst is extremely poor. Moreover, when the reaction is performed at an increased isobutane content of 28 mol %, the yield is likely to decrease. Hence, the process of U.S. Pat. No. 4,260,822 is unsatisfactory as a commercial process from the viewpoint of productivity per unit weight of the catalyst.

Thereafter, in Japanese Patent Application Laid-Open Specification No. 62-132832, a process for preparing methacrylic acid in high yield and with high productivity was proposed, which comprises reacting isobutane in a concentration as high as 30 to 60 mol %, using a heteropoly acid as a catalyst. High yield and high productivity have been realized by this process, which has extremely characteristic features in that a heteropoly acid having phosphorus as a central element and containing molybdenum is used as the catalyst, and that isobutane and oxygen are alternately contacted with the catalyst. However, a special reaction apparatus is necessary for alternately contacting isobutane and oxygen with the catalyst, and the operation of such an apparatus is complicated. Therefore, the process of the Japanese Patent Application is likely to be economically disadvantageous from the viewpoint of a commercial practice, as compared to the conventional process which comprises simply contacting a mixed gas of isobutane and oxygen with a catalyst.

Moreover, it is known that with respect to a molybdenum heteropoly acid, the structure thereof is decomposed at a temperature higher than 350° C. although the rate of the decomposition is low. Despite this fact, reaction in the above-process is carried out at a temperature of from 350° to 370° C. This is because the activity of the catalyst is insufficient and hence a low temperature reaction causes the yield to be gravely lowered. Actually, decomposition of a heteropoly acid occurs even at about 330° C. in the above reaction. Therefore, a catalyst capable of providing excellent yield even at a temperature of 320° C. or lower has been desired in the art.

More specifically, with respect to a process for preparing methacrylic acid by contacting a mixed gas of isobutane and oxygen in the vapor phase with a catalyst, an improved process which can be carried out at a temperature of 350° C. or lower, preferably 320° C. or lower to produce methacrylic acid with high productivity and in high yield while maintaining a stable activity of the catalyst over a prolonged period of time, has been strongly desired.

DISCLOSURE OF THE INVENTION

In the above-described situations, the present inventors have made extensive and intensive studies on heteropoly acid catalysts with a view toward developing a catalyst with which an excellent reaction performance is attained by simply contacting a mixed gas comprising isobutane and oxygen in the vapor phase with the catalyst at a temperature of 350° C. or lower, preferably 320° C. or lower. As a result, it has been found that methacrylic acid and methacrolein can be produced with high selectivity by simply contacting a mixed gas comprising isobutane and oxygen in the vapor phase with a specific catalyst comprising a P and/or As—Mo—V and/or Cu composition containing a heteropoly acid having P and/or As as a central element or central elements and Mo as a coordinating element, which composition is selected from among a vast plurality of elements and an almost infinite number of combinations thereof. Also, it has been found that methacrylic acid and methacrolein can be produced in high yield and with high productivity even at temperatures as low as 320° C. or lower when at least one member selected from the group consisting of an alkali metal, an alkaline earth metal and Tl is incorporated in the above-mentioned catalyst composition. In particular, it has been found that the catalyst containing at least one member selected from the group consisting of an alkali metal, an alkaline earth metal and Tl is an extremely excellent catalyst having a long catalytic life, which is not only effective in lowering reaction temperature but can also advantageously maintain the catalytic activity and methacrylic acid selectivity for a prolonged period of time. The present invention has been completed on the basis of these findings.

According to the present invention, a process for the preparation of methacrylic acid and methacrolein is provided, which comprises contacting at a temperature of from 240° to 350° C. a mixed gas comprising isobutane and molecular oxygen in the vapor phase with a catalyst comprising a composition containing a heteropoly acid having P and/or As as a central element or central elements and Mo as a coordinating element. The composition is represented by the formula:

$$A_a Mo_{12} B_b C_c D_d O_e \tag{b 1}$$

wherein A represents P and/or As; Mo represents molybdenum; B represents V and/or Cu; C represents at least one member selected from the group consisting of an alkali metal, an alkaline earth metal and Tl; D represents at least one member selected from the group consisting of Ag, Zn, Cd, Ti, Zr, Nb, Ta, Cr, W, Mn, Fe, Co, Ni, B, Al, Ge, Rh, Sn, Sb, Bi, Se, Te, Y, La, Ce, Pr and Nd; 0 represents oxygen; and a, b, c, d and e are numbers, respectively, representing relative atomic proportions of A, B, C, D and 0, wherein a, b, c and d are respectively, in the ranges of from 0.5 to 3, from 0.01 to 3, from 0 to 3 and from 0 to 3, and e is the number of oxygens required to satisfy the valence and relative atomic proportion requirements of the elements present. In the present invention, it is of critical importance to use the catalyst having the abovedefined composition. Methacrylic acid and methacrolein can be obtained in high yield and with high productivity, by contacting a mixed gas comprising isobutane and oxygen in the vapor phase with the catalyst according to the present invention. When a catalyst lacks the essential components of the above-mentioned composition, i.e., P and/or As—Mo—V and/or Cu, or when a catalyst has relative atomic proportions which are outside the ranges defined above, the selectivity for methacrylic acid markedly drops in the reaction of the process in which a mixed gas comprising isobutane and oxygen is contacted in the vapor phase with the catalyst, as apparent from Comparative Examples 1 to 14 described later.

As described in Japanese Patent Application Laid-Open Specification No. 62-132832, an oxygen seed which causes excess oxidation is likely to be formed on the surface of the catalyst in the reaction in which oxygen participates, causing methacrylic acid and methacrolein to be further oxidized, leading to a lowering in selectivity therefor. By contrast, it has unexpectedly been found that methacrylic acid is obtained with a high selectivity even in the reaction in which oxygen participates when the above-mentioned specific catalyst is used. It has not yet been fully elucidated why such unexpected effects are attained. However, it is believed that when use is made of a catalyst obtained by incorporating V and/or Cu into a P and/or As—Mo composition containing a heteropoly acid so as for the heteropoly acid to form a stable salt with the V or Cu or so as for a portion of the coordinating element of the heteropoly acid to be substituted with the V or Cu, formation of an oxygen seed, which causes the excess oxidation of methacrylic acid and methacrolein, is suppressed on the surface of the catalyst.

The reaction temperature can be lowered by the use of the catalyst according to the present invention. Thus, it is possible to carry out the reaction at a temperature at which thermal decomposition of the heteropoly acid is unlikely to occur. For improving the catalytic activity at low temperatures and to carry out the reaction at a temperature of 320° C. or lower, it is preferred that at least one member selected from the group consisting of an alkali metal, an alkaline earth metal and Tl be contained in the catalyst. In this case, the heat stability of the catalyst is also improved. By virtue of the above-mentioned reaction temperature lowering effect and heat stability improving effect, the catalyst containing at least one member selected from the group consisting of from an alkali metal, an alkaline earth metal and Tl can enjoy a long life and excellent durability. As apparent from the above, when at least one member selected from the group consisting of an alkali metal, an alkaline earth metal and Tl is used in combination with vanadium and/or copper, excellent effects are exerted, such that not only can the isobutane conversion be increased but also the reaction temperature can be lowered, while maintaining the selectivity for methacrylic acid at a high level.

Moreover, it is noted that successive oxidation of reaction products, such as methacrylic acid and methacrolein, which leads to the formation of carbon dioxide etc., is effectively suppressed by the lowering of the reaction temperature, so that the selectivity for methacrylic acid and methacrolein can be improved. In particular, when the reaction is performed in a fluid bed reactor, the reaction products are likely to suffer from excess oxidation, leading to a lowering in the selectivity for methacrylic acid as compared to the case in which a fixed bed reaction system is used. However, in the process of the present invention, a high selectivity for methacrylic acid is obtained even in the case in which a fluid bed reactor is employed since the process of the present invention can be performed at low temperatures.

Hereinbelow, the present invention will be explained in more detail. It is of critical importance that the catalyst to be employed in the present invention contain a heteropoly acid having P and/or As as a central element or central elements and Mo as a coordinating element and also contain V and/or Cu. With respect to the constituent elements of the catalyst, the relative atomic proportion of P and/or As is in the range of from 0.5 to 3 and that of V and/or Cu is in the range of from 0.01 to 3, and preferably of from 0.05 to 2.0, relative to 12 atoms of Mo. When at least one member selected from the group consisting an alkali metal, an alkaline earth metal and Tl is incorporated in the above-mentioned composition, more favorable effects can be obtained.

Examples of alkali metals include Li, Na, K, Rb and Cs, which can be used individually or in combination. Examples of alkaline earth metals include Mg, Ca, Sr and Ba, which can be used individually or in combination. The alkali metal, the alkaline earth metal and Tl are used in a relative atomic proportion of from 0.01 to 3, preferably from 0.1 to 2. Further, at least one member selected from the group consisting of Ag, Zn, Cd, Ti, Zr, Nb, Ta, Cr, W, Mn, Fe, Co, Ni, B, Al, Ge, Rh, Sn, Sb, Bi, Se, Te, Y, La, Ce, Pr and Nd is used preferably in a relative atomic proportion of from 0.01 to 3, more preferably from 0.05 to 1.

Examples of heteropoly acids having P and/or As as a central element or central elements and Mo as a coordinating element include a molybdophosphoric acid, an molybdoarsenic acid, a molybdoarsenophosphoric acid, and the like, which are known to assume various structures (see Sasaki and Matsumoto: *Kagaku no Ryoiki*, vol. 29, no. 12, page 853). For example, heteropoly acids having structures in which the ratios of central element to coordinating element are, respectively, 1/12, 1/11, 1/10, 1/9, 2/17 and 2/18 are known. Among the heteropoly acids, one having a structure in which the above-mentioned ratio is 1/12, known as the Keggin structure, is especially preferred.

It is preferred that vanadium be present in a form such that it substitutes for a portion of the coordinating element of a molybdophosphoric acid, a molybdoarsenic acid or a molybdoarsenophosphoric acid. However, a portion of the vanadium may be present in the form of a non-heteropoly acid, such as an oxide or an oxyacid. The chemical state of the copper present in the catalyst is extremely complicated, and has not yet been elucidated in detail. Copper may be present either in the form of a salt with a heteropoly acid or in the form of a non-heteropoly acid, such as an oxide and an oxyacid. Alternatively, copper may be present in a form such that it substitutes for a portion of the elements constituting the heteropoly acid. It is preferred that copper be present in the form of an oxide or a salt of a heteropoly acid. With respect to an alkali metal, an alkaline earth metal and Tl, these are mainly present in the form of a salt of a heteropoly acid. Further, as in the case of Cu described above, Ag, Zn, Cd, Ti, Zr, Nb, Ta, Cr, W, Mn, Fe, Co, Ni, B, Al, Ge, Rh, Sn, Sb, Bi, Se, Te, Y, La, Ce, Pr and Nd may be present either in the form of a salt of a heteropoly acid or in the form of a non-heteropoly acid, such as an oxide and an oxyacid. Alternatively, each of these elements may be present in a form such that it substitutes for a portion of the elements constituting the heteropoly acid.

The catalyst to be employed in the present invention can readily be prepared according to the conventional methods (preparative operations). Generally, the catalyst is prepared by first adding compounds containing necessary elements, which are in the form of an oxide, a hydroxide, a carbonate, a nitrate, a chloride, an oxyacid, a phosphate, an oxalate, an acetate, an organic complex compound or a metal, to a solution or a slurry of a heteropoly acid, such as a molybdphosphoric acid, a molybdovanadophosphoric acid, a molybdoarsenic acid or an molybdoarsenophosphoric acid, or a salt thereof, or to a place under conditions in which such a heteropoly acid is formed, subsequently performing evaporation to dryness, and finally calcining the resultant solid in an air environment at 250° to 500° C. for 2 to 24 hours. However, the method of catalyst preparation and the starting materials for use in catalyst preparation are not limited to the above. Other methods and starting materials may be used. For example, various nitrogen-containing compound salts of a heteropoly acid may be used as a starting material. Representative examples of effective salts include ammonium salts, and salts with organic amines, such as pyridine, quinoline and piperadine. These nitrogen-containing compounds may be used in the step of catalyst preparation. With respect to the ammonium salts, aqueous ammonia or water soluble ammonium salts, such as ammonium chloride and ammonium nitrate, can be added as an ammonium ion source. These ammonium salts or organic amine salts are calcined at from 300° to 600° C. to remove a portion or all of the nitrogen-containing compound, prior to use as a catalyst. Calcination is preferably performed in an inert gas. Calcination in an inert gas may be followed by calcination in an oxygen-containing gas.

These catalysts may be carried on a carrier or may be diluted and mixed with a carrier. Representative examples of carriers include silica, α-alumina, titania, zirconia, diatom earth, silica alumina, water soluble silica sol and silicon carbide. Inert carriers having a vast plurality of macropores and thus a high porosity are preferred. The catalyst is generally carried on or mixed with such a carrier, in the presence or absence of water, in an amount of up to the weight equal to the weight of the carrier.

Prior to use, the catalyst may preferably be molded into a suitable shape and a suitable size, e.g., pellet or granular shape, depending on application conditions, so as to impart a desired mechanical strength to the catalyst. In molding the catalyst, a tablet machine, an extrusion molding machine, Marumerizer (trade name of a product of Fuji Paudal, Japan), a rolling type granulator and the like may be used.

The degree of reduction at which the catalyst functions under the reaction conditions for the process fo the present invention has not completely been elucidated. However, since even the catalyst in a state of high degree of reduction often turns into a yellow-greenish color with the lapse of reaction time, not exhibiting a dark blue color known as heteropoly blue, the catalyst under the reaction conditions is considered to be in a state of a degree of reduction as low as a level corresponding to 1 or 2-electron increase per heteropoly acid or lower. The degree of reduction, however, greatly depends on the composition of the catalyst, the composition of the reaction gas and the reaction temperature. Therefore, the degree of reduction of the catalyst is not limited to the above range.

As a gaseous feedstock to be supplied to the reaction system, a mixed gas comprising isobutane and oxygen is used. The isobutane content of the mixed gas is preferably in the range of from 10 to 80% by mole. If the isobutane content is lower than 10% by mole, the amount of methacrylic acid produced per reactor is so small that productivity suited for commercial production cannot be obtained. The isobutane content is more preferably in the range of from 20 to 60 by mole. Isobutane to be used in the catalytic reaction is not necessarily of high purity, and hence a mixture in which a paraffinic hydrocarbon not adversely affecting the reaction is contained in a molar amount about two times that of isobutane may be employed. It is preferred to use isobutane isolated by distillation from LPG butane, FCC butane or a reaction product of isomerization of n-butane. If an olefin is contained in a molar amount of about 0.1 time or more that of isobutane, the formation of by-products is increased. Hence, contamination with olefins other than isobutylene is preferably to be avoided.

In the present invention, the molar ratio of oxygen to isobutane is preferably in the range of from 0.05:1 to 1:1, more preferably in the range of from 0.1:1 to 0.6:1. If the molar proportion of oxygen is higher than the above, complete oxidation occurs excessively, resulting in an increase in the formation of carbon dioxide. On the other hand, if the molar proportion of oxygen is smaller than the above, oxygen supply is not sufficient for oxidation of isobutane and the conversion of isobutane is lowered. Also, if the molar proportion of oxygen is smaller than the above, the reduction of the catalyst disadvantageously proceeds in excess with the advance of the reaction.

It is preferred that the oxygen content and isobutane content be chosen so that the composition of the resultant mixed gas may be outside an explosive range. As the molecular oxygen to be used for the catalytic reaction, pure oxygen gas may be employed. However, since it is not essential to use a molecular oxygen of high purity, the use of air is generally preferred from the economical point of view. Further, it is possible to prevent the composition of the mixed gas from falling inside the explosive range, by using, as a diluent for the mixed gas, nitrogen and other inert gases having no adverse effect on the reaction, such as helium, argon and carbon dioxide. In this case, the inert gases are generally used at a molar ratio to isobutane of from 1:10 to 10:1.

In order to prevent methacrylic acid as a reaction product from being further oxidized on the catalyst and thereby forming carbon dioxide and the like, steam is preferably added to molecular oxygen and isobutane, at a molar ratio to isobutane of from 1:5 to 5:1, thereby enhancing the selectivity for methacrylic acid. The molar ratio is more preferably in the range of from 1:3 to 3:1.

The reaction temperature is chosen in the range of from 240° to 350° C., preferably 270° to 320° C. If the reaction temperature is higher than the above, the decomposition of the catalyst and the complete oxidation of the reaction product are likely to occur. Particularly, when use is made of a catalyst having at least one member selected from the group consisting of an alkali metal, an alkaline earth metal and Tl, methacrylic acid is produced in high yield and with high productivity, even at a reaction temperature of 320° C. or lower.

The reaction pressure may be selected in a wide range from a reduced pressure to a super-atmospheric pressure. However, the pressure which is advantageous from the viewpoint of commercial production is in the range from atmospheric pressure to about 1 MPa.

The contact time (i.e., the value obtained by dividing the bulk volume of the catalyst by the volume gas flow rate of the mixed gas at the reaction temperature and the reaction pressure) of the mixed gas as a feedstock with the catalyst varies depending on the isobutane concentration and the reaction temperature. The contact time is generally from 0.1 to 10 seconds, preferably from 0.5 to 5 seconds.

In the practice of the present invention, the reactor to be used can suitably be selected from various types including a fixed bed reactor, a fluidized bed reactor and a moving bed reactor.

Methacrylic acid and methacrolein formed can be isolated from by-produced oxides by a series of customary processes, such as cooling, extraction and distillation, and purified by any of customary methods. When unreacted isobutane is recovered and recycled into the reactor, the recycled isobutane may contain reaction products, such as carbon monoxide and carbon dioxide, as long as the content of these products does not adversely affect the subsequent reaction. By feeding back methacrolein together with the feedstock mixed gas containing isobutane into the reactor, the methacrolein can be effectively converted into methacrylic acid.

BEST MODE FOR CARRYING OUT THE INVENTION

The present invention will be described in more detail with reference to the Examples, which should not be construed to be limiting the scope of the present invention.

EXAMPLES

Example 1

144.0 g of molybdenum trioxide, 8.27 g of vanadium pentoxide and 12.5 g (85% by weight) of phosphoric acid were charged into a three-neck Pyrex flask together with 1000 ml of water, and heated under reflux for 24 hours. Then, the insoluble matter in the aqueous solution was filtered off, and the solution was concentrated, thereby obtaining red-brown crystals. By analysis using X-ray diffraction, atomic absorption spectroscopy and $^{31}$PNMR, the crystals were found to be molybdovanadophosphoric acid (PMo$_{11}$V) having P:Mo:V relative atomic proportions of 1:11:1. The crystals were in the form of approximately triaconta hydrates. 23.2 g of the crystals and 0.1 g of cuprous chloride were dissolved in 200 ml of water heated to 80° C. 2.0 g of cesium nitrate dissolved in 50 ml of water was added thereto, and further 23.8 g of pyridine dissolved in 100 ml of water was added thereto, thereby obtaining a slurry. The slurry was concentrated and then dried at 120° C. for 12 hours. The resultant solid product was pulverized and particles of 10 to 20 mesh were selected, followed by calcining at 450° C. for 3 hours under a stream of nitrogen. As a result, a catalyst having a composition of $P_{1.1}Mo_{12}V_{1.1}Cu_{0.11}Cs_{1.1}$ (showing relative atomic proportions excluding that of oxygen being indicated; this being applicable to the formulae shown hereinafter) was obtained.

5 g of the catalyst was introduced into a Pyrex U-tube having an inner diameter of 6 mm and set in a thermostatic bath. The temperature of the thermostatic bath was set at 320° C., and a mixed gas consisting of 30% by mole of isobutane, 15% by mole of oxygen, 20% by mole of steam and 35% by mole of nitrogen was fed at a contact time of 3.6 seconds. When the reaction gas was analyzed by gas chromatography 100 hours after the beginning of the reaction, it was found that 10.3% of the isobutane was converted and that the selectivity for methacrylic acid was 55.7% and the selectivity for methacrolein was 16.3%. No isobutylene was detected. The reaction was performed for 1000 hours under the same conditions. As a result, 10.1% of the isobutane was converted, and the selectivity for methacrylic acid was 56.3% and the selectivity for methacrolein was 15.9%.

Example 2

In substantially the same manner for catalyst preparation as in Example 1, a catalyst having a composition of $P_{1.1}Mo_{12}V_{1.1}$ was obtained. Of the starting materials described in Example 1, cuprous chloride and cesium nitrate were not employed, and catalytic reaction was performed under substantially the same conditions as in Example 1. 20 hours after the beginning of the reaction, the reaction gas was analyzed by gas chromatography. As a result, it was found that 5.3% of the isobutane was converted, and that the selectivity for methacrylic acid was 41.1% and the selectivity for methacrolein was 19.2%.

Example 3

In substantially the same manner for catalyst preparation as in Example 1, a catalyst having a composition represented by the formula: $P_1Mo_{12}Cu_{0.5}$ was obtained. 12-Molybdophosphoric acid ($H_3PMo_{12}O_{40}\cdot 3H_2O$: produced by Nippon Inorganic Colour & Chemical Co., Ltd., Japan) was used instead of $PMo_{11}V$. Differing from Example 1, cesium nitrate was not used. Catalytic reaction was performed under substantially the same reaction conditions as in Example 1. 20 Hours later, the resultant gaseous reaction mixture was subjected to analysis by means of gas chromatography. It was found that 5.4% of isobutane was converted, and that the selectivity for methacrylic acid and the selectivity for methacrolein were 42.1% and 22.5%, respectively.

Example 4

In substantially the same manner for catalyst preparation as in Example 1, a catalyst having a composition represented by the formula: $P_1Mo_{12}V_{0.5}As_{0.1}Cu_{0.2}$ was obtained. 12-Molybdophosphoric acid ($H_3PMo_{12}O_{40}\cdot 3H_2O$: produced by Nippon Inorganic Colour & Chemical Co., Ltd., Japan) and arsenic acid ($H_3AsO_4$) were used in addition to the raw materials used in Example 1. Catalytic reaction was performed under substantially the same conditions as in Example 1 except that the reaction temperature was changed to 340° C. 20 Hours later, the resultant gaseous reaction mixture was subjected to analysis by means of gas chromatography. It was found that 10.0% of isobutane was converted and that the selectivity for methacrylic acid and the selectivity for methacrolein were 47.2% and 19.3%, respectively.

Comparative Example 1

Substantially the same procedure for catalyst preparation as in Example 1 was repeated to thereby obtain a catalyst, except that 23.2 g of 12-molybdophosphoric acid ($H_3PMo_{12}O_{40}\cdot 3H_2O$: produced by Nippon Inorganic Colour & Chemical Co., Ltd., Japan) was dissolved in 100 ml of water and that no other raw material was used. Reaction was performed under substantially the same conditions as in Example 1. 20 Hours later, the resultant gaseous reaction mixture was subjected to analysis by means of gas chromatography. It was found that 4.3% of isobutane was converted, and that the selectivity for methacrylic acid and the selectivity for methacrolein were 18.3 % and 21.1 %, respectively.

Comparative Examples 2 to 14

Substantially the same procedure for catalyst preparation process as in Example 1 was repeated to thereby obtain catalysts having the compositions shown in Table 1 which are outside the scope of the present invention. Catalytic reaction was performed under substantially the same conditions as in Example 1 except that, in certain Comparative Examples, the reaction temperature was changed as indicated in Table 1. The results after the reaction for 20 hours are shown in Table 1.

TABLE 1

| Comparative Example | Composition of catalyst | Reaction temperature °C. | Conversion of isobutane % | Selectivity for methacrylic acid % | Selectivity for methacrolein % |
| --- | --- | --- | --- | --- | --- |
| 2 | $P_{1.3}Mo_{12}$ | 340 | 10.5 | 18.3 | 21.1 |
| 3 | $P_{1.3}Mo_{12}K_2$ | 340 | 7.3 | 34.3 | 15.3 |
| 4 | $P_{1.3}Mo_{12}Cs_{1.5}$ | 340 | 8.0 | 30.2 | 17.2 |
| 5 | $P_{1.3}Mo_{12}Li_1$ | 340 | 6.9 | 27.2 | 25.3 |
| 6 | $P_{1.3}Mo_{12}As_{0.2}Mg_1$ | 340 | 8.3 | 32.5 | 18.9 |
| 7 | $P_{1.3}Mo_{12}Pb_{0.2}$ | 340 | 6.2 | 29.6 | 18.2 |
| 8 | $P_{1.3}Mo_{12}Cr_{0.5}$ | 340 | 7.8 | 26.2 | 23.2 |
| 9 | $P_{1.3}Mo_{12}Zn_{0.2}$ | 340 | 7.4 | 31.3 | 16.3 |
| 10 | $P_{1.3}Mo_{12}Sn_{0.4}$ | 340 | 7.6 | 32.2 | 18.3 |
| 11 | $P_{1.3}Mo_{12}Te_{0.2}Sr_{0.5}$ | 340 | 8.4 | 34.5 | 18.9 |
| 12 | $P_{1.3}Mo_{12}V_{0.001}Cs_1$ | 320 | 5.9 | 38.2 | 19.3 |
| 13 | $P_{1.3}Mo_{12}Cu_{0.001}K_1$ | 320 | 6.2 | 36.3 | 20.1 |
| 14 | $P_1Mo_{12}Rb_1$ | 320 | 5.8 | 30.1 | 24.5 |

Example 5

23.6 g of crystal 12-molybdophosphoric acid ($H_3PMo_{12}O_{40}\cdot 3H_2O$: produced by Nippon Inorganic Colour & Chemical Co., Ltd., Japan), 0.1 g of cuprous chloride and 0.85 g of arsenic acid ($H_3AsO_4$) were dissolved in 200 ml of water to obtain a solution. Then, to the solution were added 8.0 g of pyridine and 100 ml of water, and the resultant mixture was thoroughly stirred. The thus obtained slurry was concentrated and then dried at 120° C. for 12 hours, followed by pulverization. From the resultant powder, particles of from 10 to 20 mesh were collected. The particles were calcined under a nitrogen stream at 450° for 3 hours and subsequently in the air at 350° C. for 2 hours, thereby obtaining a catalyst having a composition represented by the formula: $PMo_{12}As_{0.6}Cu_{0.1}$.

Reaction was performed in substantially the same manner as in Example 1, except that the reaction temperature was changed to 340° C. 6 Hours later, the gaseous reaction mixture was subjected to analysis by means of gas chromatography. It was found that 8.8% of isobutane was converted, and that the selectivity for methacrylic acid and the selectivity for methacrolein were 46.2% and 25.1%, respectively. The catalyst after completion of the reaction was yellow-green.

Example 6

Substantially the same procedure as in Example 5 was repeated except that antimony trioxide was added instead of arsenic acid, and that 13 g of quinoline was added instead of pyridine, thereby obtaining a catalyst having a composition represented by the formula: $P_1Mo_{12}Cu_{0.5}Sb_{0.5}$.

Using the catalyst, a reaction was performed in substantially the same manner as in Example 1 except that the reaction temperature was changed to 340° C. As a result, it was found that 9.1% of isobutane was converted, and that the selectivity for methacrylic acid and the selectivity for methacrolein were 42.3% and 19.4%, respectively.

Example 7

236.5 g of 12-molybdophosphoric acid and 11.5 g of $3As_2O_5\cdot 5H_2O$ were dissolved in water at 60° C. for 12 hours while stirring, thereby obtaining 1000 ml of a solution. To 150 ml of the solution were added 14.5 g of crystal molybdovanadophosphoric acid, 0.18 g of a 85% by weight aqueous phospholic acid solution and 100 ml of water, and the resultant mixture was stirred for 2 hours. Then, 100 g of a 6.4% by weight aqueous ammonium nitrate solution was added thereto to obtain a slurry. The slurry was concentrated and then dried at 120° C. for 12 hours, followed by pulverization. From the resultant powder, particles of from 10 to 20 mesh were collected. The particles were calcined under a nitrogen stream at 450° C. for 3 hours and subsequently in the air at 350° C. for 2 hours, thereby obtaining a catalyst having a composition represented by the formula: $P_{1.1}Mo_{12}V_{0.30}As_{0.64}$. Using the catalyst, a reaction was performed in substantially the same manner as in Example 1 except that the reaction temperature was changed to 340° C. 6 Hours later, the resultant gaseous reaction mixture was subjected to analysis by means of gas chromatography. It was found that 8.3% of isobutane was converted, and that the selectivity for methacrylic acid and the selectivity for methacrolein were 46.8% and 22.5%, respectively.

Examples 8 to 26

Substantially the same procedure for catalyst preparation as in Example 1 was repeated to thereby obtain catalysts having compositions shown in Table 2. Reaction was performed in substantially the same manner as in Example 1, except that the reaction temperature was changed to 340° C. The results after the reaction for 20 hours are shown.

| Example | Composition of catalyst | Conversion of isobutane % | Selectivity for methacrylic acid % | Selectivity for methacrolein % |
|---|---|---|---|---|
| 8 | $P_{1.3}Mo_{12}V_{0.6}Ag_{0.1}$ | 7.5 | 48.3 | 22.3 |
| 9 | $P_{1.3}Mo_{12}V_{0.6}Zn_{0.1}$ | 7.6 | 50.2 | 15.6 |
| 10 | $P_1Mo_{12}V_{1.5}Fe_{0.1}$ | 7.0 | 46.0 | 15.0 |
| 11 | $P_2Mo_{12}V_1Co_{0.1}$ | 7.0 | 46.8 | 14.5 |
| 12 | $P_{1.3}Mo_{12}V_1Ni_{0.1}$ | 7.1 | 48.2 | 10.5 |
| 13 | $P_{1.2}Mo_{12}V_{1.5}Al_{0.2}$ | 6.8 | 46.2 | 9.5 |
| 14 | $P_{1.3}Mo_{12}V_1Ge_{0.5}Fe_{0.1}$ | 8.0 | 49.3 | 16.4 |
| 15 | $P_{1.3}Mo_{12}V_1Zr_{0.1}$ | 7.1 | 48.2 | 12.9 |
| 16 | $P_1Mo_{12}Cu_{0.5}W_{0.1}$ | 8.9 | 40.3 | 16.1 |
| 17 | $P_{1.3}Mo_{12}Cu_{0.1}Ta_{0.1}$ | 7.4 | 42.2 | 12.5 |
| 18 | $P_1Mo_{12}Cu_{0.1}Te_{0.1}$ | 8.1 | 43.2 | 14.3 |
| 19 | $P_1Mo_{12}Cu_{0.1}Rh_{0.1}$ | 7.2 | 44.2 | 16.3 |
| 20 | $P_1Mo_{12}Cu_{0.1}Se_{0.1}$ | 6.9 | 46.3 | 13.5 |
| 21 | $P_1Mo_{12}Cu_{0.1}Mn_{0.3}$ | 7.4 | 41.5 | 16.3 |
| 22 | $P_1Mo_{12}As_{0.6}Cu_{0.1}Nb_{0.3}$ | 7.7 | 46.3 | 15.4 |
| 23 | $P_1Mo_{12}V_1Cu_{0.1}Ce_{0.5}$ | 9.2 | 54.6 | 17.1 |
| 24 | $P_1Mo_{12}V_{1.9}Cu_{0.1}Nd_{0.1}$ | 8.6 | 55.6 | 18.2 |
| 25 | $P_1Mo_{12}V_1Cu_{0.1}As_{0.3}B_{0.1}$ | 8.8 | 56.2 | 19.2 |
| 26 | $P_1Mo_{12}V_1Cu_{0.1}Bi_{0.1}$ | 8.2 | 51.1 | 18.3 |

Example 27

200 ml of water was heated to 80° C., and 23.5 g of 12-molybdophosphoric acid ($H_3PMo_{12}O_{40}\cdot 30H_2O$: produced by Nippon Inorganic Colour & Chemical Co., Ltd., Japan) was dissolved therein. To the resultant solution were added a solution prepared by dissolving 1.0 g of potassium nitrate and 0.48 g of copper nitrate in 20 ml of water and 1.17 g of ammonium metavanadate in this order while stirring. Then, to the resultant solution was added a solution prepared by dissolving 6.4 g of ammonium nitrate in 100 ml of water to obtain a slurry. The thus obtained slurry was concentrated while heating and stirring, then evaporated to dryness using an evaporating dish, and dried at 120° C. for 12 hours to obtain a solid. The solid was calcined at 450° C. for 3 hours to obtain a catalyst. The catalyst had a composition represented by the formula: $P_1Mo_{12}V_1Cu_{0.2}K_1$.

5 g of the catalyst was introduced into a pyrex U-tube having an inner diameter of 6 mm, and the U-tube was set in a thermostatic bath. While maintaining the temperature of the bath at 300° C., a mixed gas consisting of 25% by mole of isobutane, 55% by mole of air and 20% by mole of steam was fed into the U-tube at a flow rate such that the contact time of the gas with the catalyst was 3.6 seconds. 100 Hours later, the gaseous reaction mixture was subjected to analysis by means of gas chromatography. It was found that 7.8% of isobutane was converted, and that the selectivity for methacrylic acid and the selectivity for methacrolein were 53.4% and 20.8%, respectively. No isobutylene was detected. A reaction was separately performed for 1,000 hours under substantially the same conditions as above. It was found that 7.5% of isobutane was converted and that the selectivity for methacrylic acid and the selectivity for methacrolein were 54.4% and 21.1%, respectively.

Example 28

23.5 g of 12-molybdophosphoric acid ($H_3PMo_{12}O_{40}\cdot 30H_2O$: produced by Nippon Inorganic Colour & Chemical Co., Ltd., Japan) was dissolved in 200 ml of water. To the resultant solution were added 0.37 g of sodium metavanadate and 1.15 g of $3As_2O_5\cdot 5H_2O$ while stirring, and then the mixture was stirred at 60° C. for 12 hours. To the resultant solution were added a solution prepared by dissolving 0.5 g of rubidium nitrate and 1.33 g of thallium nitrate in 20 ml of water and an aqueous solution prepared by dissolving 12.8 g of ammonium nitrate in 100 ml of water in this order. The mixture was stirred to obtain a slurry. The thus obtained slurry was concentrated while heating and stirring, then evaporated to dryness using an evaporating dish, and dried at 120° C. for 12 hours to obtain a solid. The solid was pelletized under a pressure of about 100 kg/cm$^2$, and then pulverized. From the resultant powder, particles of from 10 to 20 mesh were collected. The particles were calcined under a nitrogen stream at 450° C. for 3 hours to obtain a catalyst. The catalyst had a composition represented by the formula: $P_1Mo_{12}V_{0.3}As_{0.64}Rb_{0.5}Tl_{0.5}$.

5 g of the catalyst was introduced into a pyrex U-tube having an inner diameter of 6 mm, and the U-tube was set in a thermostatic bath. While maintaining the temperature of the bath at 340° C., a mixed gas consisting of 30% by mole of isobutane, 50% by mole of air and 20% by mole of steam was fed into to the U-tube at a flow rate such that the contact time of the gas with the catalyst was 3.6 seconds. 100 Hours later, the gaseous reaction mixture was subjected to analysis by means of gas chromatography. It was found that 10.8% of isobutane was converted, and that the selectivity for methacrylic acid and the selectivity for methacrolein were 45.8% and 18.2%, respectively. No isobutylene was detected. A reaction was separately performed under substantially the same conditions as above except that the reaction time was changed to 500 hours. It was found that 9.9% of isobutane was converted, and that the selectivity for methacrylic acid and the selectivity for methacrolein were 47.2% and 19.3%, respectively.

Example 29

23.5 g of 12-molybdophosphoric acid ($H_3PMo_{12}O_{40} \cdot 30H_2O$: produced by Nippon Inorganic Colour & Chemical Co., Ltd., Japan) was dissolved in water. To the resultant solution was added 0.85 g of arsenic acid ($H_3AsO_4$), followed by stirring at 60° C. for 12 hours. To the resultant solution were added 0.24 g of copper nitrate and a solution prepared by dissolving 2.66 g of thallium nitrate and 1.31 g of barium nitrate in 40 ml of water in this order. Then, to the resultant solution was added a solution prepared by dissolving 13.7 g of pyridine in 100 ml of water. The resultant mixture was stirred to obtain a slurry. The thus obtained slurry was concentrated while heating and stirring, then evaporated to dryness using an evaporating dish, and dried at 120° C. for 12 hours to obtain a solid. The solid was pelletized under a pressure of about 100 kg/cm$^2$, and then pulverized. From the resultant powder, particles of from 10 to 20 mesh were collected. The particles were calcined at 450° C. for 3 hours to obtain a catalyst. The catalyst had a composition represented by the formula: $P_1Mo_{12}As_{0.6}Cu_{0.1}Tl_1Ba_{0.5}$.

5 g of the catalyst was introduced into a pyrex U-tube having an inner diameter of 6 mm, and the U-tube was set in a thermostatic bath. While maintaining the temperature of the bath at 340° C., a mixed gas consisting of 60% by mole of isobutane, 20% by mole of oxygen and 20% by mole of steam was fed into the U-tube at a flow rate such that the contact time of the gas with the catalyst was 3.6 seconds. 100 Hours later, the gaseous reaction mixture was subjected to analysis by means of gas chromatography. It was found that 9.5% of isobutane was converted, and that the selectivity for methacrylic acid and the selectivity for methacrolein were 44.2% and 17.4%, respectively. No isobutylene was detected. A reaction was separately performed for 500 hours under substantially the same conditions as above. It was found that 9.4% of isobutane was converted, and that the selectivity for methacrylic acid and the selectivity for methacrolein were 43.3% and 17.1%, respectively.

Examples 30 to 42

In substantially the same manner for catalyst preparation as in Example 1, catalysts having the compositions shown in Table 3 were obtained. Reaction was performed in substantially the same manner as in Example 1 except that the reaction temperature was changed to 340° C. The results after the reaction for 100 hours are shown in Table 3.

TABLE 3

| Example | Composition of catalyst | Conversion of isobutane % | Selectivity for methacrylic acid % | Selectivity for methacrolein % |
|---|---|---|---|---|
| 30 | $P_{1.3}Mo_{12}V_{0.2}K_1$ | 11.2 | 45.8 | 15.4 |
| 31 | $P_{1.5}Mo_{12}V_{0.5}Cs_{0.2}$ | 9.5 | 47.4 | 18.2 |
| 32 | $P_1Mo_{12}V_{1.5}Mg_{0.3}$ | 9.2 | 47.2 | 19.3 |
| 33 | $P_2Mo_{12}V_2As_{0.1}Rb_{1.5}Sr_{0.1}$ | 10.9 | 46.2 | 17.3 |
| 34 | $P_{1.3}Mo_{12}V_1Cs_1Na_{0.1}$ | 11.6 | 44.3 | 14.8 |
| 35 | $P_{1.3}Mo_{12}V_{1.5}Cs_2$ | 9.0 | 46.8 | 16.3 |
| 36 | $P_{1.3}Mo_{12}Cu_{0.1}Rb_1$ | 12.4 | 44.8 | 17.6 |
| 37 | $P_{1.3}Mo_{12}Cu_{0.2}Tl_{0.5}Ca_{0.5}$ | 11.6 | 42.3 | 15.3 |
| 38 | $P_1Mo_{12}Cu_{0.5}Co_{0.1}Rb_{0.5}$ | 10.0 | 44.3 | 18.9 |
| 39 | $P_{1.3}Mo_{12}Cu_{0.1}Li_{0.1}Rb_{0.3}$ | 13.7 | 41.2 | 12.5 |
| 40 | $P_2Mo_{12}Cu_1As_{0.6}Tl_{1.5}$ | 10.6 | 44.5 | 19.8 |
| 41 | $P_{1.3}Mo_{12}Cu_{0.1}As_{0.2}Cs_1$ | 10.8 | 46.2 | 17.2 |

TABLE 3-continued

| Example | Composition of catalyst | Conversion of isobutane % | Selectivity for methacrylic acid % | Selectivity for methacrolein % |
|---|---|---|---|---|
| 42 | $P_{1.3}Mo_{12}Cu_{0.5}Mg_{0.5}Ba_{0.5}$ | 8.4 | 42.3 | 15.5 |

Examples 43 to 56

Catalysts having the compositions shown in Table 4 were prepared. Reaction was performed in substantially the same manner as in Example 1. The results after the reaction for 100 hours are shown in Table 4.

TABLE 4

| Example | Composition of catalyst | Conversion of isobutane % | Selectivity for methacrylic acid % | Selectivity for methacrolein % |
|---|---|---|---|---|
| 43 | $P_{1.2}Mo_{12}V_1Ag_{0.25}K_1$ | 8.6 | 44.6 | 16.2 |
| 44 | $PMo_{12}V_{1.5}Ag_{0.1}As_{0.25}K_1$ | 10.2 | 46.5 | 18.2 |
| 45 | $P_{1.3}Mo_{12}V_1Sb_{0.1}Cs_1$ | 7.8 | 50.2 | 22.2 |
| 46 | $PMo_{12}V_{0.8}Zr_{0.3}Cs_1$ | 7.2 | 48.9 | 16.6 |
| 47 | $PMo_{12}V_1Te_{0.25}K_1$ | 7.6 | 50.2 | 18.2 |
| 48 | $PMo_{12}V_1Ta_{0.5}B_{0.1}Rb_1$ | 8.5 | 50.6 | 22.3 |
| 49 | $P_2Mo_{12}V_1Ge_{0.5}K_1$ | 8.2 | 45.6 | 19.8 |
| 50 | $PMo_{12}Cu_{0.1}As_{0.6}Rb_1$ | 7.0 | 45.6 | 17.2 |
| 51 | $PMo_{12}Cu_{0.2}Cr_{0.1}Cs_1$ | 7.1 | 44.3 | 20.2 |
| 52 | $PMo_{12}Cu_{0.5}Ti_{0.1}K_{0.5}$ | 6.9 | 43.8 | 21.2 |
| 53 | $PMo_{12}Cu_{0.2}Fe_{0.1}Sr_{0.2}K_1Cs_{0.5}$ | 6.8 | 46.2 | 19.8 |
| 54 | $PMo_{12}Cu_{0.1}Ni_{0.3}Ca_1Tl_{0.5}$ | 6.9 | 43.2 | 18.3 |
| 55 | $PMo_{12}Cu_{0.1}Co_{0.1}Y_{0.1}Cs_1$ | 7.2 | 45.6 | 19.6 |
| 56 | $P_{1.2}Mo_{12}Cu_{0.1}Sn_{0.1}Rb_{0.25}Cs_{0.25}Tl_{0.5}$ | 7.8 | 46.3 | 18.6 |

Examples 57 to 71

Catalysts having the compositions shown in Table 5 were prepared. Catalytic reaction was performed under substantially the same conditions as in Example 1. The results after the reaction for 100 hours are shown in Table 5.

TABLE 5

| Example | Composition of catalyst | Conversion of isobutane % | Selectivity for methacrylic acid % | Selectivity for methacrolein % |
|---|---|---|---|---|
| 57 | $PMo_{12}V_1Cu_{0.2}Tl_{0.5}Rb_{0.5}$ | 11.8 | 56.2 | 15.4 |
| 58 | $PMo_{12}V_{0.5}Cu_{0.2}Zn_{0.1}K_1$ | 10.9 | 52.4 | 16.8 |
| 59 | $PMo_{12}V_{1.5}Cu_{0.2}Rh_{0.1}Cs_1$ | 9.8 | 53.2 | 14.9 |
| 60 | $PMo_{12}V_1Cu_{0.5}Nb_1Mn_{0.5}Tl_1$ | 10.1 | 53.8 | 17.2 |
| 61 | $PMo_{12}V_1Cu_{0.2}W_{0.1}K_1$ | 9.7 | 49.3 | 16.8 |
| 62 | $PMo_{12}V_{1.2}Cu_{0.1}Bi_{0.2}Tl_{0.5}K_1$ | 10.3 | 50.2 | 16.3 |
| 63 | $P_{1.3}Mo_{12}V_1Cu_{0.2}Se_{0.1}K_{1.5}$ | 10.2 | 51.1 | 17.3 |
| 64 | $PMo_{12}V_1Cu_{0.2}Al_{0.1}Tl_1$ | 11.5 | 53.2 | 14.4 |
| 65 | $PMo_{12}V_1Cu_{0.2}As_{0.1}B_{0.1}Rb_{0.5}$ | 12.8 | 50.3 | 14.2 |
| 66 | $PMo_{12}V_{0.8}Cu_{0.2}Pr_{0.5}Rb_1$ | 10.6 | 57.8 | 14.2 |
| 67 | $P_{1.5}Mo_{12}V_1Cu_{0.2}Nd_{0.5}Cs_1$ | 12.8 | 53.8 | 15.9 |
| 68 | $PMo_{12}V_1Cu_{0.2}La_{0.5}Cs_{0.5}Tl_{0.5}$ | 11.9 | 54.4 | 15.3 |
| 69 | $PMo_{12}V_1Cu_{0.2}Ca_{0.5}Rb_{0.5}$ | 10.8 | 53.4 | 16.9 |

TABLE 5-continued

| Example | Composition of catalyst | Conversion of isobutane % | Selectivity for methacrylic acid % | Selectivity for methacrolein % |
|---|---|---|---|---|
| 70 | $PMo_{12}V_1Cu_{0.1}Ce_{0.5}Cs_{0.5}Tl_{0.5}$ | 11.2 | 54.9 | 15.6 |
| 71 | $PMo_{12}V_1Cu_{0.2}Co_{0.1}Rb_{0.5}Tl_{0.5}$ | 9.7 | 50.0 | 18.2 |

Example 72

Using the catalyst $(PMo_{12}V_1Cu_{0.1}Ce_{0.5}Cs_{0.5}Tl_{0.5})$ prepared in Example 70, catalytic reaction was continuously performed for 1,000 hours under substantially the same conditions as in Example 1. It was found that the catalyst was not deteriorated, and that the conversion of isobutane, the selectivity for methacrylic acid and the selectivity for methacrolein were 10.9%, 56.3% and 15.3%, respectively.

Example 73

The catalyst $(PMo_{12}V_1Cu_{0.2}As_{0.1}B_{0.1}Rb_{0.5})$ prepared in Example 65 was introduced into a U-tube of SUS steel having an inner diameter of 6 mm. A mixed gas of 25% by mole of isobutane, 55% by mole of air and 20% by mole of steam was reacted at 280° C. under a pressure of 0.3 MPa for a contact time with the catalyst of 3.6 seconds. 100 Hours later, the resultant gaseous reaction mixture was subjected to analysis by means of gas chromatography. It was found that 6.2% of isobutane was converted, and that the selectivity for methacrylic acid and the selectivity for methacrolein were 50.3% and 22.4%, respectively. A separate catalytic reaction was continuously performed for 1,000 hours under substantially the same conditions as above. It was found that the catalyst was not deteriorated, and that the conversion of isobutane, the selectivity for methacrylic acid and the selectivity for methacrolein were 6.1%, 51.1% and 20.9%, respectively.

Example 74

Using the catalyst $(PMo_{12}V_{1.2}Cu_{0.1}Bi_{0.2}Tl_{0.5}K_1)$ prepared in Example 62, catalytic reaction was performed under substantially the same conditions as in Example 72. 100 Hours later, the resultant gaseous reaction mixture was subjected to analysis by means of gas chromatography. It was found that 6.0% of isobutane was converted, and that the selectivity for methacrylic acid and the selectivity for methacrolein were 48.2% and 24.5%, respectively. A separate catalytic reaction was continuously performed for 3,000 hours under substantially the same conditions as above. No deterioration of the catalyst was observed, and the conversion of isobutane, the selectivity for methacrylic acid and the selectivity for methacrolein were 6.0%, 47.1% and 23.8%, respectively.

Example 75

To an aqueous solution of molybdovanadophosphoric acid were added cuprous chloride, thallium nitrate and rubidium nitrate, thereby obtaining a slurry. The slurry was concentrated and evaporated to dryness, followed by drying at 130° C. for 10 hours. Then, the dried product was pulverized to obtain a powder having a composition represented by the formula: $PMo_{12}V_1Cu_{0.2}Tl_{0.5}Rb_{0.5}$. Separately, silica beads of from 100 to 200 mesh (micro bead silica gel 1,000A: produced by Fuji Debison, Japan) were calcined at 700° C. for 3 hours and then impregnated with boric acid and arsenic acid. The impregnated beads were calcined at 500° C. for 2 hours to obtain a carrier of silica having 0.03% by weight of B and 0.03% by weight of As carried thereon. A small amount of water was applied to the carrier, thereby wetting the carrier with the water. 100 g of the wetted carrier was placed on a rotating dish of a rolling type granulator, and 100 g of the above-mentioned powder was sprinkled over the carrier. Mixing was performed for 1 hour, thereby obtaining a carrier having the powdery composition penetrated deeply in the pores thereof and thus carried thereon. The resultant composite was impregnated with pyridine and then dried at 120° C. Subsequently, the dried composite was calcined under a nitrogen stream at 450° C. for 3 hours and further in the air at 350° C. for 1 hour to obtain a catalyst. Reaction was performed at 320° C. in the presence of this catalyst using a fluidized-bed reactor having an internal volume of 400 ml while feeding a mixed gas of 30% by mole of isobutane, 50% by mole of air and 20% by mole of steam at a linear velocity of 20 cm/sec for a contact time of 3.6 seconds. 20 Hours later, the gaseous reaction mixture was subjected to analysis by gas chromatography. It was found that 9.8% of isobutane was converted, and that the selectivity for methacrylic acid and the selectivity for methacrolein were 48.3% and 17.5%, respectively.

Example 76

The catalyst $(PMo_{12}V_1Cu_{0.1}Ce_{0.5}Cs_{0.5}Tl_{0.5})$ as prepared in Example 70 was molded into granules having a diameter of 1 mm and a length of 5 mm using an extrusion molding machine. The granules were charged into a fixed bed reactor of SUS steel having an inner diameter of 15 mm and a height of 1.8 m. Through the mantle of the reactor, a heat transfer medium heated at 320° C. was circulated. To the reactor was fed a mixed gas of 30% by mole of isobutane, 15% by mole of oxygen, 20% by mole of steam and 35% by mole of nitrogen for a contact time of 3.6 seconds. The reaction pressure was maintained at 0.4MPa. 100 Hours later, the gaseous reaction mixture was subjected to analysis by gas chromatography. It was found that 10.3% of isobutane was converted, and that the selectivity for methacrylic acid and the selectivity for methacrolein were 55.2% and 17.3%, respectively. Thereafter, a mixed gas of 30% by mole of isobutane, 0.6% by mole of methacrolein, 15% by mole of oxygen, 20% by mole of steam and 34.4% by mole of nitrogen was reacted. Methacrolein used in the above reaction was prepared by introducing the gaseous reaction mixture formed in the reaction into a quenching tower and then into a methacrolein absorber tower in this order, isolating methacrolein from the resultant condensed liquid and the resultant absorbed liquid, and purifying the isolated methacrolein. As compared to the case where no methacrolein was supplied, the conversion of isobutane was decreased and found to be 9.0%; however, the selectivity for methacrylic acid was improved and found to be 65.2%. About 60% of methacrolein was converted to methacrylic acid.

INDUSTRIAL APPLICABILITY

According to the process of the present invention, it is possible to produce methacrylic acid and methacrolein in one step at low cost from isobutane which is abundant and available at low cost. Moreover, the catalyst to be used in the present process maintains the catalytic activity stably for a prolonged period of time. Therefore, the process of the present invention is extremely advantageous from the viewpoint of commercial production of methacrylic acid.

We claim:

1. A process for the preparation of methacrylic acid and methacrolein, which comprises contacting at a temperature of 240° to 350° C. in a reactor a mixed gas comprising isobutane and molecular oxygen in the vapor phase with a catalyst comprising a composition containing a heteropoly acid having P and/or As as a central element or central elements and Mo as a coordinating element, said composition being represented by the formula:

$$A_a Mo_{12} B_b C_c D_d O_e \tag{1}$$

wherein A represents P and/or As; Mo represents molybdenum; B represents V and/or Cu; C represents at least one member selected from the group consisting of an alkali metal, an alkaline earth metal and Tl; D represents at least one member selected from the group consisting of Ag, Zn, Cd, Ti, Zr, Nb, Ta, Cr, W, Mn, Fe, Co, Ni, B, Al, Ge, Rh, Sn, Sb, Bi, Se, Te, Y, La, Ce, Pr and Nd; O represents oxygen; and a, b, c, d and e are numbers, respectively, representing relative atomic proportions of A, B, C, D and O, wherein a, b, c and d are, respectively, in the ranges of from 0.5 to 3, from 0.01 to 3, from 0 to 3 and from 0 to 3, and e is the number of oxygens required to satisfy the valence and relative atomic proportion requirements of the elements present, thereby obtaining a gaseous reaction mixture comprising methacrylic acid and methacrolein.

2. The process according to claim 1, wherein the index c of formula (1) is in the range of from 0.01 to 3.

3. The process according to claim 1 wherein the index d of formula (1) is in the range of from 0.01 to 3.

4. The process according to claim 1, wherein B of formula (1) is V.

5. The process according to claim 1, wherein B of formula (1) is Cu.

6. The process according to claim 1, wherein said alkali metal is at least one member selected from the group consisting of Li, Na, K, Rb and Cs.

7. The process according to claim 1, wherein said alkaline earth metal is at least one member selected from the group consisting of Mg, Ca, Sr and Ba.

8. The process according to claim 1, wherein the index b of formula (1) is in the range of from 0.05 to 2.

9. The process according to claim 2, wherein the index c of formula (1) is in the range of from 0.1 to 2.

10. The process according to claim 3, wherein the index d of formula (1) is in the range of from 0.05 to 1.

11. The process according to claim 2, wherein said temperature is in the range of from 270° to 320° C.

12. The process according to claim 1, wherein said gas has an isobutane content of from 10 to 80% by mole.

13. The process according to claim 12, wherein the isobutane content of the gas is in the range of from 20 to 60% by mole.

14. The process according to claim 1, wherein the molar ratio of oxygen to isobutane in the gas is in the range of from 0.05:1 to 1:1.

15. The process according to claim 14, wherein the molar ratio of oxygen to isobutane in the gas is in the range of from 0.1:1 to 0.6:1.

16. The process according to claim 1, wherein said gas contains steam.

17. The process according to claim 16, wherein the molar ratio of steam to isobutane in the gas is in the range of from 1:5 to 5:1.

18. The process according to claim 17, wherein the molar ratio of steam to isobutane in the gas is in the range of from 1:3 to 3:1.

19. The process according to claim 1, wherein the contact time for the contacting of said gas with said catalyst is from 0.1 to 10 seconds.

20. The process according to claim 19, wherein the contact time for the contacting of said gas with said catalyst is from 0.5 to 5 seconds.

21. The process according to claim 1, wherein said gas contains an inert gas.

22. The process according to claim 1, wherein the methacrylic acid is separated from said gaseous reaction mixture, and the methacrolein is recycled to the reactor together with the unreacted isobutane.

* * * * *